(12) United States Patent
Molnar

(10) Patent No.: US 8,092,426 B2
(45) Date of Patent: *Jan. 10, 2012

(54) REGIONAL ANESTHESIA SYSTEM AND CART

(76) Inventor: James M. Molnar, Wyoming, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/896,405

(22) Filed: Oct. 1, 2010

(65) Prior Publication Data

US 2011/0021912 A1    Jan. 27, 2011

Related U.S. Application Data

(63) Continuation-in-part of application No. 12/114,634, filed on May 2, 2008, now Pat. No. 7,806,862.

(51) Int. Cl.
*A61M 5/00* (2006.01)
*A61M 1/00* (2006.01)

(52) U.S. Cl. ......... 604/116; 604/118; 604/151; 600/439

(58) Field of Classification Search ............ 604/30, 604/116, 118, 151–153, 181, 182; 600/439, 600/554; 606/130, 439
See application file for complete search history.

(56) References Cited

U.S. PATENT DOCUMENTS

| | | | |
|---|---|---|---|
| 4,756,706 A | 7/1988 | Kerns et al. |
| 5,053,002 A | 10/1991 | Barlow |
| 5,180,371 A | 1/1993 | Spinello |
| 5,234,406 A | 8/1993 | Drasner et al. |
| 5,268,624 A | 12/1993 | Zanger |
| 5,472,416 A | 12/1995 | Blugerman et al. |
| 5,580,347 A | 12/1996 | Reimels |
| 5,647,373 A | 7/1997 | Paltieli |
| 5,700,147 A | 12/1997 | Mills et al. |
| 5,810,765 A | 9/1998 | Oda |
| 5,830,151 A | 11/1998 | Hazdic et al. |
| 6,022,337 A | 2/2000 | Herbst et al. |
| 6,055,458 A | 4/2000 | Cochran et al. |
| 6,113,574 A | 9/2000 | Spinello |
| 6,179,829 B1 | 1/2001 | Bisch et al. |
| 6,200,289 B1 | 3/2001 | Hochman et al. |

(Continued)

OTHER PUBLICATIONS

PCT International Search Report and Written Opinion for PCT/US2009/042292 dated Dec. 16, 2009 (10 pages).

(Continued)

*Primary Examiner* — Jackie Ho
*Assistant Examiner* — Leah Stohr
(74) *Attorney, Agent, or Firm* — Hasse & Nesbitt LLC; Ronald J. Richter; Donald E. Hasse

(57) ABSTRACT

A regional anesthesia system and a cart for aiding in the placement of a regional anesthesia block without the need of ancillary assistance. The invention includes equipment for use in the performance of a regional anesthesia block which is carried on a cart for transporting and providing a stable foundation for the equipment. The equipment includes a nerve localization means such as ultrasound or a peripheral nerve stimulator for locating a target nerve of a patient, a position assist arm for maintaining the position of the localization means over the target nerve while the operator inserts an anesthetic needle over the target nerve, and an anesthetic infusion device for infusing or aspirating through the anesthesia needle. The infusion device includes an infusion pump controlled by a foot pedal. The system may be easily transported to a patient requiring a regional anesthesia block, and allows the regional anesthesia block to be performed with minimal ancillary assistance.

16 Claims, 4 Drawing Sheets

U.S. PATENT DOCUMENTS

| | | |
|---|---|---|
| 6,419,654 B1 | 7/2002 | Kadan |
| 6,428,510 B1 | 8/2002 | Kadan |
| 6,428,517 B1 | 8/2002 | Hochman et al. |
| 6,464,682 B1 | 10/2002 | Snoke |
| 6,485,426 B2 | 11/2002 | Sandhu |
| 6,520,928 B1 * | 2/2003 | Junior .............................. 604/30 |
| 6,652,482 B2 | 11/2003 | Hochman et al. |
| 6,663,202 B2 | 12/2003 | Spann |
| 6,663,569 B1 | 12/2003 | Wilkins et al. |
| 6,676,669 B2 | 1/2004 | Charles et al. |
| 6,716,167 B1 | 4/2004 | Henderson et al. |
| 6,726,658 B2 | 4/2004 | Hochman |
| 6,786,885 B2 | 9/2004 | Hochman et al. |
| 6,807,965 B1 | 10/2004 | Hickle |
| 6,866,648 B2 | 3/2005 | Hazdic et al. |
| 6,887,216 B2 | 5/2005 | Hochman et al. |
| 6,905,482 B2 | 6/2005 | Hochman |
| 6,942,637 B2 | 9/2005 | Cartledge et al. |
| 6,945,954 B2 | 9/2005 | Hochman et al. |
| 6,962,581 B2 | 11/2005 | Thoe |
| 6,966,899 B2 | 11/2005 | Hochman et al. |
| 7,022,082 B2 | 4/2006 | Sonek |
| 7,311,691 B2 | 12/2007 | Cartledge et al. |
| 2002/0013640 A1 | 1/2002 | Phoon et al. |
| 2002/0016569 A1 | 2/2002 | Critchlow et al. |
| 2002/0096845 A1 * | 7/2002 | Spann ......................... 280/79.2 |
| 2003/0167021 A1 | 9/2003 | Shimm |
| 2005/0236940 A1 | 10/2005 | Rockoff |
| 2007/0129634 A1 * | 6/2007 | Hickey et al. ................. 600/439 |

OTHER PUBLICATIONS

PCT International Preliminary Report on Patentability for PCT/US2009/042292 dated Nov. 2, 2010 (4 pages).

* cited by examiner

REGIONAL ANESTHESIA SYSTEM AND CART

CROSS REFERENCE TO RELATED APPLICATION

This application is a continuation-in-part of application Ser. No. 12/114,634, filed May 2, 2008 now U.S. Pat. No. 7,806,862.

FIELD OF THE INVENTION

The present invention relates generally to devices and methods for performing regional anesthesia, and more particularly to a regional anesthesia system and a cart for making the system transportable.

BACKGROUND OF THE INVENTION

Regional anesthesia (RA) procedures and, in particular, peripheral nerve blocks for surgical anesthesia and postoperative analgesia, are typically performed for pain relief during and after surgical procedures. RA is typically used for labor, chronic pain, in epidural, subdural or spinal procedures, and for plexus blocks and blocks of peripheral nerves (e.g. axillary and interscalene blocks of the brachial plexus, femoral nerve, sciatic nerve and popliteal nerve blocks). Peripheral nerve blocks, when properly performed, can be superior to general anesthesia, as they can provide effective analgesia with few side effects and can hasten patient recovery.

RA is typically performed in a separate block-placement area or in the operating room. Typically the anesthesiologist or practitioner performing the block requires ancillary staff to assist in the procedure (e.g. localizing the nerve with an ultrasound probe, holding an ultrasound probe in place over the nerve, holding and injecting the local anesthetic, etc.) while the practitioner carefully inserts the needle and then holds the needle in place at the injection site. Indeed, successful block placement has often required the use of three, four or more hands. Most practitioners require nurses to be present to perform some of the duties, such as pushing the local anesthetic solution of choice through a syringe and needle placed at the injection site, once the needle has been stabilized over the nerve of interest by the practitioner. This need for "another set of hands" can be a disadvantage, as "feel" is important to the practitioner for knowing if the needle is in the right place.

Historically, due to comparatively unreliable success rates and often time-consuming block placement procedures, RA has been thought of as a second choice to general anesthesia, and often is performed only if necessary. The clinical practice of regional anesthesia has thus been limited by inherent difficulties that to date may only be overcome with expertise in the area. Proper RA practice necessitates significant hands-on clinical experience, along with a strong commitment to improve one's skills to achieve success. RA requires a working knowledge of anatomy and superior hand dexterity in order to reliably accomplish numerous tasks, generally on a conscious, nervous and/or fidgety patient. Such tasks typically include localization of a target nerve, localization of an injection site, appropriate placement of a needle at the injection site, stabilization of the needle, infusion of medication(s), and monitoring a response. All of these steps require significant training, time and commitment. Often the time constraints of busy surgical centers have limited the application of RA even further.

Although uncommon, the risks of RA include nerve injury, permanent nerve damage, intravascular injection of local anesthetic resulting in systemic toxicity, and pneumothorax (e.g. following supraclavicular block). However, these risks can be minimized by proper localization of the target nerve and placement of the needle at the injection site, followed by controlled infusion of the local anesthetic.

While successful block of a target nerve typically depends upon accurate placement of local anesthetic in sufficient amounts around the nerve, locating the target nerve has often proved problematical in patients with difficult landmarks. Utilization of new technology, such as evoking parathesias and using peripheral nerve stimulators (PNS) or ultrasound for localization, has typically been haphazard and can often further complicate the process rather than simplify it. The techniques of evoking parathesias and peripheral nerve stimulation are essentially "blind" procedures, since they rely on indirect evidence of needle-to-nerve contact. Seeking nerves by trial and error and random needle movement can cause complications. Therefore, proper peripheral nerve stimulation for nerve localization, while holding promise for improving block success and decreasing complications, requires clinical experience and should only be used by trained individuals. Unfortunately, typically only one "trained individual" is present for the placement of the nerve block (i.e. an anesthesiologist, nurse anesthetist or other practitioner), and this individual only has two hands where often many hands are required simultaneously.

With the advent and introduction of ultrasound into clinical practice of RA, these issues have only become more compounded. Trying to position and prep the patient, use PNS or an ultrasound probe to find the nerve, determine an injection site close to the nerve, place the needle at the injection site, and inject the medication while maintaining the needle position during injection can be very difficult to master without a well-trained ancillary staff. However, increasing demands are often placed upon regional anesthesia practitioners such that extra personnel are not always available to assist the practitioner perform the procedures. Further, sometimes situations occur where it would be beneficial if the procedure were performed in a cramped space at the patient's bedside, where only one individual has adequate access to the patient. There are also situations in which the practitioner must move quickly from one surgical suite to another in order to perform blocks on multiple patients over a short period of time. In such situations, it would be beneficial if the practitioner were able to perform the needed RA procedures alone, or with minimal ancillary assistance. It would also be helpful if the practitioner had sufficient supplies and equipment that were also able to travel with him from one surgical suite to another. In such situations a mobile medical cart has often come in handy.

There are many examples in the prior art of mobile or portable medical carts. For example, U.S. Pat. No. 6,663,569 to Wilkins et al. discloses a portable ultrasound cart holding the electronic circuitry of the ultrasound system, a control panel for controlling the system, and a display. The control panel has an articulating mechanism enabling an adjustable height to accommodate the height of the practitioner, and also enabling the control panel to be moved forward and backward to accommodate users in both the sitting and standing positions. U.S. Pat. No. 6,419,654 to Kadan discloses a diagnostic needle and arthroscopy lavage system that includes a cart for housing a video monitor, a camera, an optic and light system, a VCR, an air compressor, an irrigation pump, suction unit, collection canisters and an arthroscope. U.S. Pat. No. 5,712,482 to Gaiser et al. discloses a portable cart-based electronic imaging system wherein an X-ray screen is mounted on the cart by a manipulable arm assembly enabling selective positioning movement of the screen horizontally, vertically, and angularly to receive the radiation beam.

While prior art medical carts may be useful for their intended purposes, currently there is no medical cart available that provides all of the equipment and supplies typically required for performing a successful RA block with little or no assistance. To date, no integrated means or system exists to assist with the many steps required for successfully performing a regional nerve blockade. Thus, it would be desirable to provide a system for aiding the RA practitioner in the steps of nerve localization, needle placement, needle stabilization, and medication infusion with minimal or no ancillary assistance. It would also be advantageous to have an infusion device that can provide feedback to the practitioner regarding the injection rate, resistance to injection, and pressure profile of the medication. It would also be desirable if such equipment were available on a cart for quickly and easily transporting the equipment to the block-placement area.

SUMMARY OF THE INVENTION

The present invention provides a dedicated regional anesthesia (RA) system that can be combined with a transportable cart for aiding a practitioner of RA in the performance of a peripheral nerve block, including the steps of nerve localization, needle placement, needle stabilization and medication infusion, with minimal or no ancillary assistance.

A first aspect of the invention provides a system for use in the placement of a regional anesthesia block without the need of ancillary assistance, the system comprising: (a) a nerve localization means for assisting an operator in locating a target nerve of a patient; (b) a position assist arm for maintaining the position of the localization means over the target nerve once the target nerve has been located; (c) an infusion device adapted to control anesthetic medication flow through a regional anesthesia needle; (d) a foot pedal for controlling the flow of anesthetic medication through the infusion device; and (e) a cart for transporting the system from one area of a hospital or medical center to the room of a patient requiring a regional anesthesia block, wherein the combination of the nerve localization means, the position assist arm, the infusion device and the foot pedal allows the operator to be free to use both hands for manipulating the anesthesia needle during the regional anesthesia block procedure.

A second aspect of the invention provides a transportable regional anesthesia blockade system for performing a regional anesthesia block procedure, comprising: (a) an ultrasound imaging system to assist an operator in locating a target nerve, the ultrasound imaging system including a central processing unit and an ultrasound transducer probe; (b) a position assist arm for maintaining the position of the ultrasound transducer probe over the target nerve once the target nerve has been located; (c) an infusion device for controlling anesthetic medication flow through a regional anesthesia needle, the infusion device including flexible tubing which leads from the infusion device to the anesthesia needle; (d) a foot pedal for powering the infusion device, the foot pedal including a coupling cable which leads from the foot pedal to the infusion device; and (e) a cart for transporting the system from one area of a hospital or medical center to the room of a patient requiring a regional anesthesia block, wherein the combination of the ultrasound imaging system, the position assist arm, the infusion device and the foot pedal allows the operator to be free to use both hands for manipulating the anesthesia needle during the regional anesthesia block procedure.

A third aspect of the invention provides a method of performing a regional anesthesia blockade procedure with no ancillary assistance, the method comprising the steps of: (a) providing a transportable regional anesthesia blockade system to an operator, the system comprising an ultrasound imaging system to aid in locating a target nerve, a position assist arm for maintaining the position of the ultrasound imaging system over the target nerve once the target nerve has been located, an infusion device for controlling anesthetic medication flow through a regional anesthesia needle, a foot pedal for powering the infusion device, and a cart for transporting the system within a hospital or medical center to the room of a patient requiring a regional anesthesia block; (b) transporting the transportable regional anesthesia blockade system via the cart to the patient; (c) locating a target nerve of the patient via the ultrasound imaging system; (d) stabilizing the ultrasound imaging system over the located target nerve by affixing the ultrasound imaging system to the position assist arm; (e) inserting a regional anesthesia needle into an injection site at or near the target nerve; and (f) operating the foot pedal to inject medication from the infusion device through the regional anesthesia needle and into the injection site.

As explained in more detail below, the system of the invention typically includes a nerve localization means to aid the operator in the localization of the target nerve, which may improve the chances for success in patients with difficult landmarks. For example, an ultrasound imaging system or a peripheral nerve stimulator (PNS) device can be used to help the operator locate the target nerve. A PNS device works by forwarding an electrical stimulus to the anesthesia needle, which can then stimulate the target nerve either via motor or sensory nerve stimulation. While useful, nerve stimulators can be misleading and unreliable when information about position of the needle tip in relation to the nerve substance is sought.

Ultrasonography sends high frequency sound of specific frequency ranges through tissues. Penetration into tissue is based in large part on the range of the frequency produced. Ultrasound scanning of deep abdominal organs such as liver, gallbladder, and kidneys requires low-frequency probes (3-5 MHz). Scanning superficial structures such as the brachial plexus, on the other hand, requires high-frequency probes (10-15 MHz) that provide high axial resolution; however, beam penetration is limited to 3 to 4 cm. A lower-frequency probe (4-7 MHz) is suited for scanning deeper structures, such as the brachial plexus in the infraclavicular region and the sciatic nerve in adults. An ultrasound probe (transducer) has dual functions. It emits and receives sound waves, thus functioning both as a "speaker" and a "microphone." As the sound passes through tissues it is either absorbed, reflected or allowed to pass through, depending on the density ("echo"-density) of the tissue. Typically the "listening" part of the probe (a piezo-electric crystal not unlike the generating part of the probe) listens for reflections (echoes) of the sound waves sent out and passes the information to a processing unit.

Perhaps the most significant advantage of ultrasound technology is the ability to provide anatomic examination of the area of interest in real-time. Ultrasound imaging allows one to simultaneously visualize neural structures (plexus and peripheral nerves) and the surrounding structures (e.g., blood vessels and pleura), navigate the needle toward the target nerves, and visualize the pattern of local anesthetic spread. In this manner, ultrasonography can improve the accuracy, success, and safety of regional anesthesia blocks.

The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

The present invention provides a regional anesthesia blockade system that can be combined with a transportable cart for aiding a practitioner of regional anesthesia in the performance of a regional anesthesia block or peripheral nerve block.

As defined herein, the term "aspirate" means to remove or withdraw a liquid (e.g. a solution, blood, or medication) backwards through a needle. Aspiration creates negative pressure in the system, and when performing a regional anesthesia block aspiration is typically done by the practitioner prior to injection of local anesthetic in order to ensure that needle placement and injection is not intravascular.

The term "infuse" means to inject or introduce a liquid (e.g. a solution, blood, or medication) forward through a needle by applying positive pressure, typically for therapeutic purposes.

The term "infusion device" means an anesthetic delivery device such as an electronic infusion pump, a mechanical pump or other controller used to accurately regulate the flow rate and/or monitor the pressure of local anesthetic or medication passing through a regional anesthesia needle. Typically an infusion device is able to electronically monitor the pressure and sound an alarm should an unsafe occurrence be detected relating to the infusion.

Figure 1:
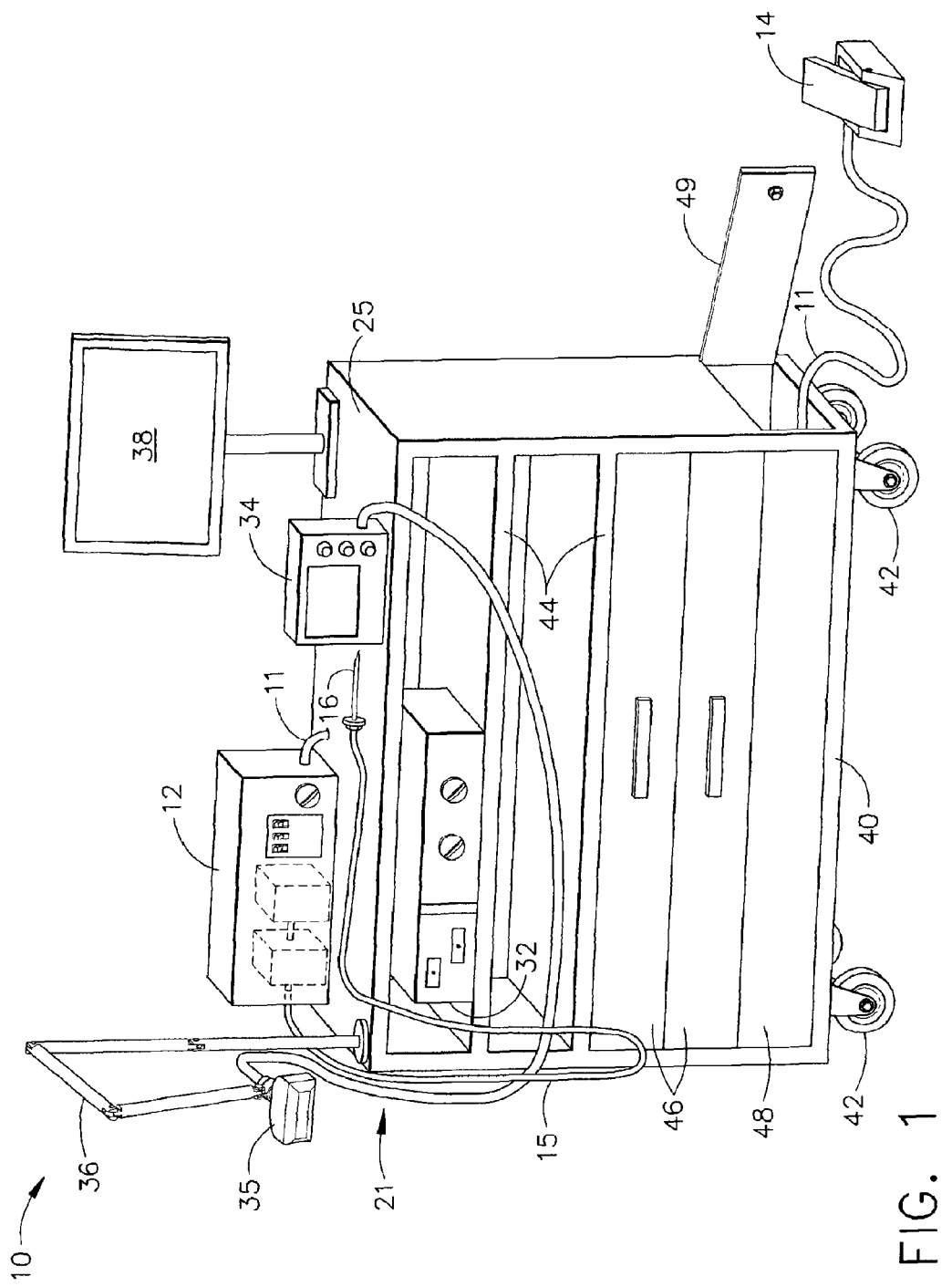
FIG. 1 is a perspective view of one embodiment of the cart and components of the regional anesthesia blockade system of the present invention.

FIG. 1 shows a regional anesthesia blockade system 10 in accordance with the invention for aiding the medical practitioner in performing a regional anesthesia block procedure. As illustrated, the system 10 includes an electronic infusion device 12 adapted to control anesthetic medication flow through a regional anesthesia needle 16. A foot pedal 14, adapted for powering the infusion device 12, functions via a coupling cable 11 which leads from the foot pedal 14 to the infusion device 12, and flexible tubing 15 leads from the infusion device 12 to the anesthesia needle 16. A control module 32 can be included to control and/or pre-program the cooperation between the infusion device 12 and the foot pedal 14. The system also includes a nerve localization means, typically an ultrasound imaging system having a central processing unit 34 and ultrasound transducer probe 35, to aid the operator in the localization of the target nerve. Advantageously, the system includes a position assist arm 36 which can be used for maintaining the position of the probe 35 or other localization means, such as a peripheral nerve stimulator device (not shown), over a target nerve once the target nerve has been localized by the operator, thereby allowing the operator to be free to use both hands for the remainder of the block procedure.

The system 10 is typically transportable by way of a cart 21, which typically includes a base 40, a plurality of lockable wheels 42 for supporting the base 40 and making the cart transportable, and a plurality of shelves 44 and drawers 46 for housing regional anesthesia equipment and other supplies. A lower compartment 48 has a door 49 for access thereto, and can be used to store the foot pedal 14 and its coupling cable 11 when not in use. The cart 21 allows the system 10 of the invention to be easily transported from room to room, for example within a hospital or surgical center, or to a patient requiring a regional anesthesia block.

As illustrated in FIG. 1, the cart 21 includes a top surface 25 which can permanently carry the position assist arm 36 as well as a video display device, such as a monitor 38. Typically the monitor 38 is able to swivel for easy viewing, and can be slaved/coupled/connected to the ultrasound device 34, the electronic infusion device 12, or other equipment such as an EKG monitor, a blood pressure cuff, a pulse oximeter and/or a peripheral nerve stimulator to provide a real-time, easy-to-view display for the practitioner during placement of the block. For example, the monitor 38 can be coupled with the ultrasound processor/probe 34, 35 to display a visual image of the target nerve. The top surface 25 of the cart 21 can also be used as a work surface by the practitioner for preparing the necessary items required for a particular blockade procedure. The wheels 42 can be locked to create a stable foundation for the top surface 25 during use.

Figure 2:
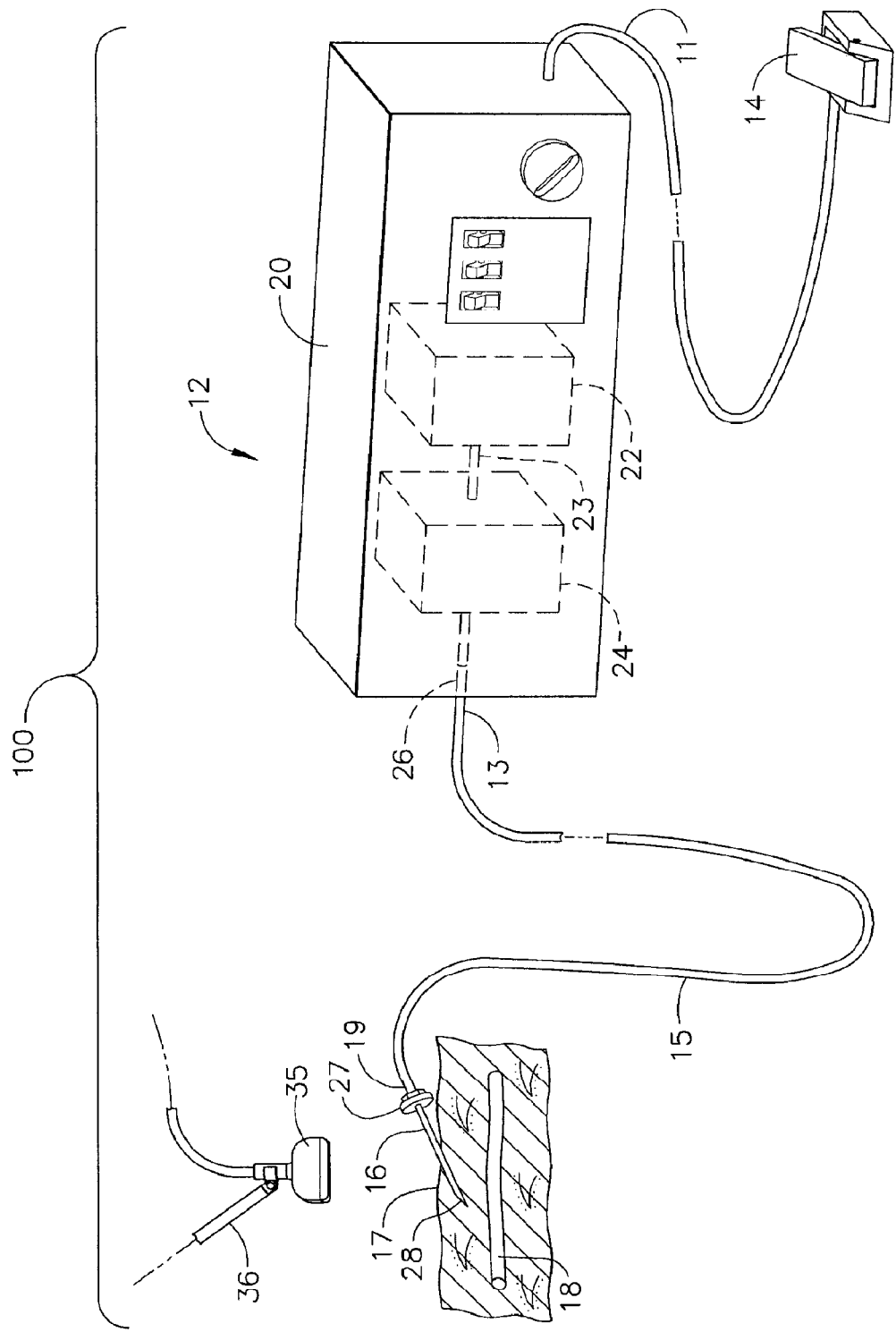
FIG. 2 is a perspective view of one embodiment of an anesthesia infusion device for use with the regional anesthesia blockade system of the present invention.

FIG. 2 shows a schematic view of one embodiment 100 of the system of the invention, which includes the ultrasound probe 35 for assisting in locating the target nerve 18 of the patient, the position assist arm 36 maintaining the position of the probe 35 over the target nerve 18, and the infusion device 12 adapted to control anesthetic medication flow through the regional anesthesia needle 16.

Typically the infusion device 12 includes an infusion pump 24 in combination with the operator-controlled foot pedal 14. The infusion device 12 typically includes a housing 20, a local anesthetic storage compartment 22 for storing and allowing access to a local anesthetic, connective tubing 23 for accessing the local anesthetic within the storage compartment 22, and the pump 24 or other anesthetic flow means, such as a peristaltic rotary device, configured to create the desired flow of local anesthetic from the storage compartment 22, through the tubing 23, and through an output end 26. The pump 24 ultimately causes anesthetic medication in the infusion device 12 to flow through the regional anesthesia needle 16. The foot pedal 14 typically controls the flow rate and pressure output of the infusion pump 24. The operator controls the foot pedal 14, and can control and modify the flow of anesthetic medication through the needle by simple up and down movement of the foot pedal 14.

The pump 24 can be a peristaltic rotary flow/aspiration pump or the like, but can also be a device known in the art for creating and controlling the desired flow of local anesthetic. Other suitable anesthetic flow means which are known in the art can perform the function of the infusion device 12, and include, as a non-limiting example, pump mechanisms having either a direct drive/screw system, pump mechanisms having a peristaltic or rotary action, magnetic drive systems, syringes and the like, so long as they can be controlled by an operator via a foot-operated pedal 14.

The infusion device 12 is typically adapted to electronically cause local anesthetic to flow through the needle 16 upon depression of the foot pedal 14 by the practitioner, and to sound an alarm should a hazardous event be detected relating to the infusion. The foot pedal 14 is connected via coupling cable 11 to the infusion device 12, and the coupling cable 11 is typically between about 4 feet to about 15 feet in length, to allow the pedal to reach the practitioner during placement of the block. In use, typically an anesthetic block needle 16 is inserted by an operator trained in performing regional anesthesia blocks, and is inserted at an injection site 17 adjacent to or in the vicinity of a target nerve 18 for which a nerve block is desired. An ultrasound device 35 and position assist arm 36, as described above, can be used by the practitioner to locate and maintain the location of the target nerve 18. The output end 26 of the infusion device 12 is adapted to be fitted or attached via the flexible tubing 15, the flexible tubing in turn having an input end 13 and an output end 19. As illustrated, the output end 19 of the flexible tubing 15 is attached to the input end 27 of the regional anesthesia needle 16. Needle 16 has an output end 28 for delivering local anesthetic to the injection site 17 near or proximate the target nerve 18 of the patient.

The control module 32 (FIG. 1) can be associated with the infusion device 12 and can include an infusion control for data entry for the pump 24, such as setting the parameters of operation (drug concentration, drug volume, rate limits, pressure limits, etc.), and a pedal control for controlling operation of the foot pedal 14 in accordance with the parameters set by the infusion control. The parameters set by the control module 32 can be set to patient-specific rate and pressure ranges before the block is performed. Further, pre-set parameters can also include basic rate limits and pressure limits specific to certain block procedures, such as parameters for a typical axillary block, interscalene block, femoral block, etc. Custom parameters can also be set for specific patients. Thus, the control module 32 can control operation of the infusion device 12 in response to depression of the foot pedal 14 and in accordance with the parameters set by the infusion control.

The infusion device 12 is typically set to function at infusion pressures of between about 10 pounds per square inch (psi) to about 20 psi, and at an infusion rate of between about 5 ml/min to about 15 ml/min. Infusion pressures greater than 20 psi are known to cause nerve injury, and pressures less than 10 psi may mean the needle is not in the neuro-vascular sheath, and thus too far from the nerve to cause blockade. Pressures of less than 1 psi typically mean that the needle is most likely inside a vein and should be immediately withdrawn to avoid intravascular injection. Pressures greater than 25 psi likely mean the needle is intra-neural and should be withdrawn to prevent nerve injury; however, both PNS and ultrasound nerve localization means may be able to clarify needle placement.

The infusion device will typically operate via a continuous flow rate of an operator-selectable nature, and can be programmed to allow the pump to maintain a certain injection pressure by automatically adjusting the flow rate to allow consistent and homogeneous spread of local anesthetic around the nerve pathway. As indicated above, a flow rate of between about 5 ml/min to about 15 ml/min is preferred and will typically limit too rapid of an infusion. These flow rates reflect acceptable guidelines of administering local anesthetic at a slow rate (typically 30 ml over 3-5 min.) to minimize the chance of reaching excessive blood levels of local anesthetic. At these safe flow rates, flow pressures typically range from about 5 psi to about 15 psi. However, when infusion pressures reach an unacceptable level, such as greater than 20 psi (or a lower pressure limit designated by the user), the pump can be programmed to sound an alarm and then slow, stop, or prevent initiation of infusion at any rate, to avoid nerve damage from a possible intra-neural injection. The foot pedal can also provide some feedback (e.g. tactile, visual or audio) to the operator regarding increasing resistance to flow with increasing pressurization of injection. As is known in the art, the infusion device 12 can include means for monitoring pressures during injection and sounding an alarm should excessive pressures or speeds of injection beyond the preset infusion rate occur.

In operation, the operator need not occupy his hands to operate the infusion device 12. Rather, the pump mechanism or other anesthetic flow means of the infusion device 12 is powered by the foot pedal 14, and local anesthetic is then caused to flow from the anesthetic storage compartment 22, through the connective tubing 23 and out through the output end 26. The anesthetic then flows through the flexible tubing 15, through the needle 16, and is injected at the injection site 17 near the target nerve 18 of the patient, to produce the nerve block (see FIG. 2). In one embodiment, the connective tubing 23 and the flexible tubing 15 can be a single tubing connecting to the local anesthetic stored in the storage compartment 22.

Figure 3:
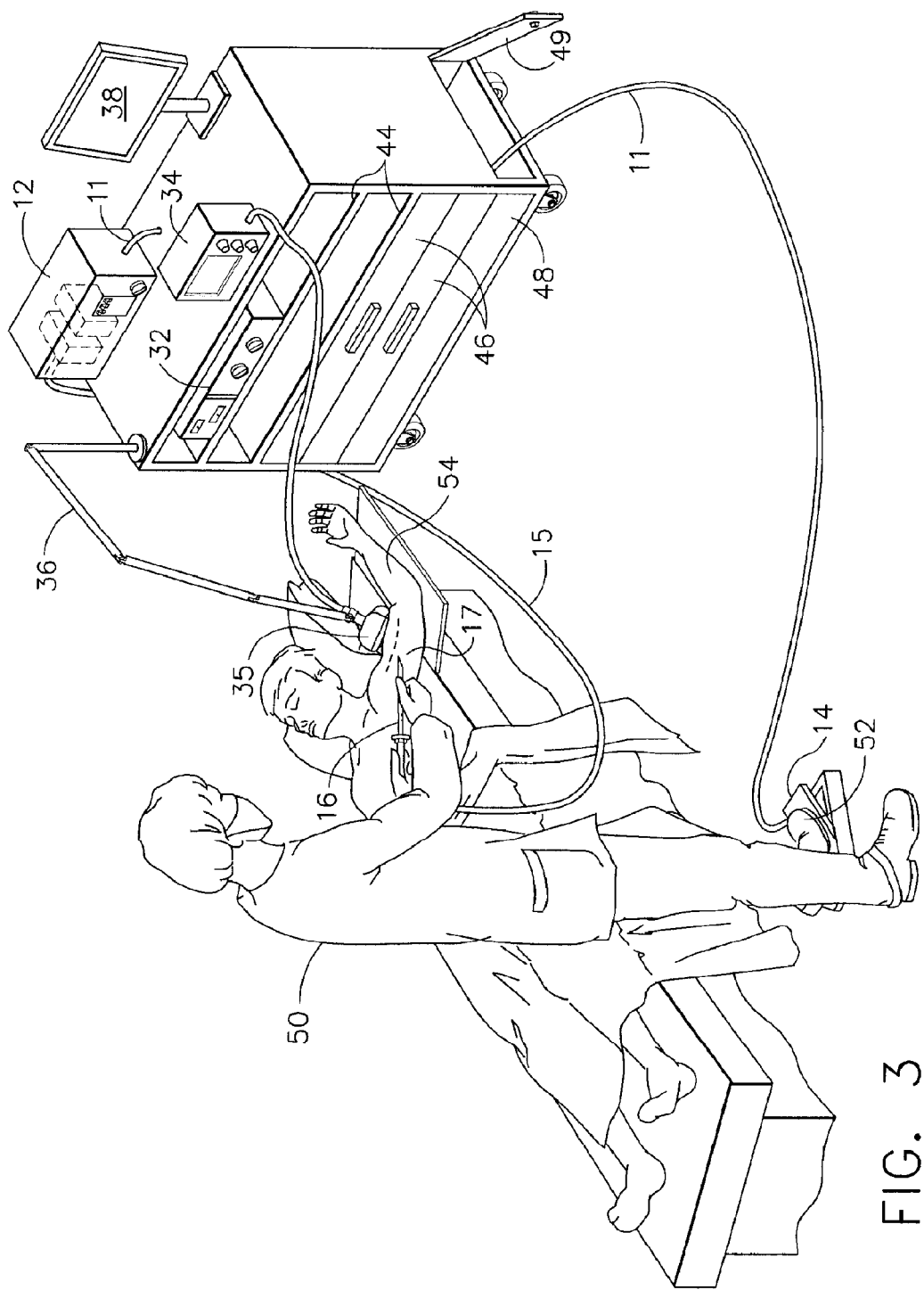
FIG. 3 shows a regional anesthesia blockade system in accordance with the invention.

FIG. 3 shows a practitioner 50 performing an axillary blockade procedure on a patient 54 while powering the infusion device 12 by depressing the foot pedal 14. As illustrated, the practitioner 50, having already located the target nerve via the ultrasound probe 35 which has been affixed by the assist arm 36 over the target nerve, inserts the end of the needle 16 at the injection site 17 and uses the foot pedal 14 to control the infusion device 12 by means of his foot 52. The control module 32 can be used, and is typically programmed ahead of time to control the operation of the infusion device 12 in response to depression of the foot pedal 14. The infusion device 12 then controls the flow of local anesthetic medication through the regional anesthesia needle 16. Depression of the foot pedal 14 causes infusion to begin, and the rate of infusion typically varies linearly with the amount of depression of the foot pedal 14 up to the maximum infusion rate. Release of the foot pedal 14 by the practitioner's foot 52 typically causes infusion to end. It can be appreciated that the use of the foot pedal 14 allows the nerve block to be performed by the practitioner 50 in a more facile manner than previously possible, because the practitioner does not have to rely on an assistant to help in performance of the various steps of the procedure.

In addition to causing infusion to vary linearly with the amount of depression, the foot pedal 14 can incorporate "viscoelastic" properties, so that increasing pedal depression is associated with tactile feedback of increasing resistance/force. Visual or auditory feedback can also be provided via a pressure monitor or digital/LED readouts that can be viewed on the monitor 38 (see FIG. 1). Further, the foot pedal 14 can include a "negative mode" which is able to initiate the infusion pump to aspirate or create negative pressure in the system, in order to ensure that needle placement and injection is not intravascular. That is, if the needle has been placed inside a blood vessel, then depression of the foot pedal in the negative mode will cause aspiration of blood through the needle, syringe and tubing, which would be an indication to the operator that the needle should be immediately removed and repositioned at a new injection site around the target nerve to avoid intravascular injection of local anesthetic. The negative mode can be initiated by a separate button or bar on the foot pedal, or else movement of the foot pedal in the opposite direction from injection to cause aspiration.

Figure 4:
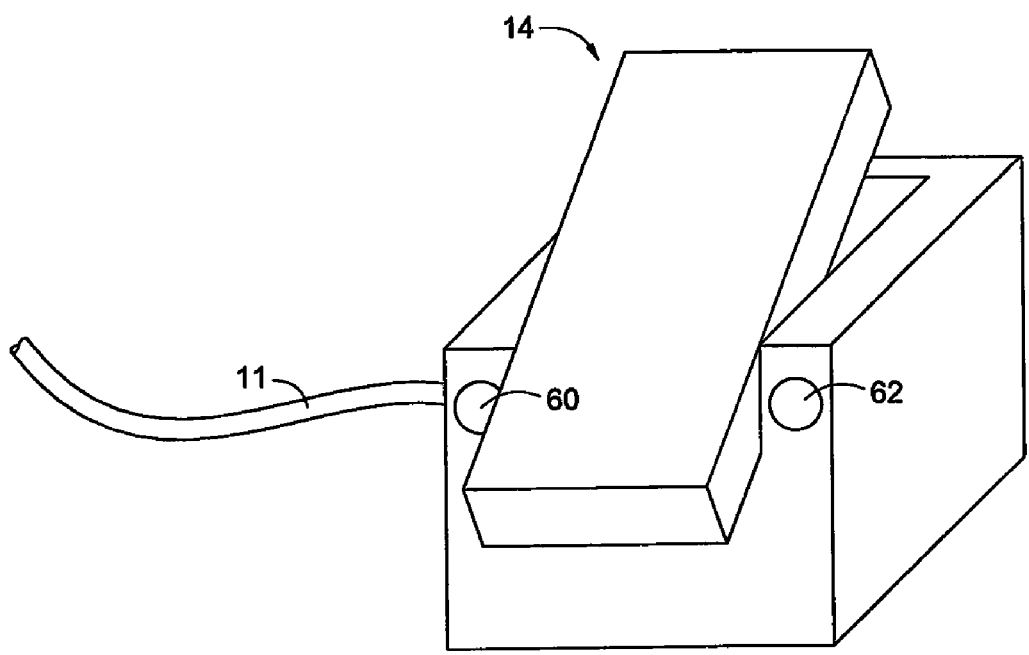
FIG. 4 illustrates an event button and a picture button located on a foot pedal.

The foot pedal can also be configured to include an "event button" as illustrated in FIG. 4. The event button 60 is a push button that can be pushed to record what the practitioner regards as a significant event during the block procedure.

Activation of the event button 60 can cause the production of a printed readout recording, for example, the injection rate, resistance to injection, and pressure profile of the medication at the time of the event, as well as patient vital signs and other significant information. The foot pedal 14 of FIG. 4 can also be equipped with a "picture button" which is another push button 62 that can be activated by the practitioner's foot to capture a digital photograph of the ultrasound image during the event. In this manner, significant events can be recorded and photographed by the push of a button on the foot pedal. If a PNS device is used to locate the target nerve, the foot pedal can also be adapted to control the strength of the PNS device, so that the target nerve can be located more easily and safely.

The system and cart of the present invention allows the operator to perform a regional anesthesia block without the need for an assistant. The foot pedal performs one of the duties of an assistant by allowing the operator to control and modify the flow of local anesthetic medication through the regional anesthesia needle, thereby leaving the operator's hands free for placing the regional anesthesia needle in the correct position at the injection site. Local anesthetics typically used with the system of the invention include, but are not limited to, Xylocalne® (lidocaine), Marcaine®/Sensorcaine® (bupivacaine), Carbocaine® (mepivacaine) and Naropin® (ropivacaine). As a non-limiting example, typical dosages include lidocaine 1% or 2% (with or without epinephrine), mepivacaine 1%, 1.5%, or 2% (with or without epinephrine), and bupivacaine 0.25% or 0.5% (with or without epinephrine).

Due to the potential for untoward physiological effects when an anesthetic block is performed on a patient, emergency airway equipment should be immediately available at all times on the regional anesthesia cart of the invention. In order to comply with current safety standards, the system will typically include modern acute care equipment such as a mask valve ventilation device (Ambu bag) with an oxygen source, an end-tidal $CO_2$ detector, a suction apparatus, pulse oximetry, vital sign monitors including a blood pressure monitoring apparatus, and EKG (electrocardiogram) tracing equipment. Further, the cart will have drawers for storing emergency supplies that may be necessary during the performance of a regional anesthesia block, such as oral airways of various sizes, tongue depressors, laryngeal mask airways, nasal airways, laryngoscope equipment with an assortment of commonly used blades, and styletted endotracheal tubes of various sizes. Respiratory rate must also be monitored throughout the block procedure, and can be stored in the drawers and cabinets of the cart. These items ideally should be a part of the nerve block cart for immediate access and availability. Further, to perform successful nerve block anesthesia, appropriate needles, syringes, and the ancillary equipment necessary for the block should also be available. Further, a sharps disposal container and a small discard boxes are typically attached to the cart.

A thorough and ergonomically prepared regional block tray is a prerequisite for successful and time-efficient administration of regional blocks, and can also improve safety. Unless the operator has all equipment prepared and ready to use, the performance of the block may become quite laborious. Regional anesthesia trays can be set up in many different ways, and with the present invention such a tray can be conveniently set up on the top work surface 25 of the cart 21 (see FIG. 1). A basic setup typically includes a small instrument tray and a pack of sterile surgical towels for covering the tray. As a non-limiting example, the tray can be arranged to include sterile gloves, sterile 4×4 gauze, 10-20 ml syringes, local anesthetic, a skin marker with a ruler, electrodes for a nerve stimulator, an insulated nerve stimulator needle of desired length, a 25 G 1½ inch needle for skin infiltration, and solution for skin preparation. While this is a common setup for a nerve-stimulator assisted nerve block, other equipment that is typically used with various blocks may be added, such as stopcocks, various block needles, control syringes, extension tubing etc. Emergency medications should be organized and placed in an immediately accessible location throughout the nerve block procedure.

It is understandable that there may be variations in personal preferences as to which equipment and medications the regional anesthesia cart of the invention should contain and how it should be organized. However, it is intended that the cart be organized and stocked in such a way that just about any regional block procedure can be performed, and in a time-efficient manner in the block area, on the patient ward, or in the operating room. Such a cart could improve the comfort and success rates of regional anesthesia practitioners performing regional block, and eliminate or reduce the need for the practitioner to require the services of a nurse or assistant during the procedure.

The present invention simplifies the difficult process of performing a regional anesthetic blockade, including the complex steps of nerve localization, needle placement, needle stabilization, and medication infusion. The integration on a single apparatus of a position assist arm for holding a PNS device and/or an ultrasound device along with an infusion device and foot pedal allows a regional anesthesia block to be performed with minimal ancillary assistance. The cart of the invention can easily transport these devices to a patient requiring a regional anesthesia block. Both the position assist arm and the infusion device with its foot pedal leave the operator's hands free to provide more stable needle placement and stabilization during injection of the medication, thus providing for the safe infusion of medication. Therefore, the invention advantageously simplifies the steps of the block placement process which are typically difficult to perform unassisted.

While nursing personnel and other ancillary assistants may still be present and available, the invention makes them available to attend to patient care and comfort, rather than to block placement procedural needs such as aspirating the needle or injecting and adjusting the ultrasound or PNS devices. The invention can greatly enhance the performance and safety of regional anesthesia applications by minimizing the time for block placement, enhancing safety monitoring, and standardizing infusion protocols. The invention can greatly reduce the concerns of time-consuming and/or inadequate nerve blockade, reduce costs, lead to broader application of RA in the surgical care of patients, and provide greater patient safety and satisfaction. Further, printer capability can be added to communicate with the other electronic modules of the cart, and an electronic report of the block event can be generated (as noted above in the description of the foot pedal), thereby improving the time consumption, legibility and accuracy of typical hand-written reports.

In addition to the elements listed above, the present invention can include a portable battery for use either as backup when there is no standard electrical outlet available, or as a main source of power for all of the elements on the cart, and thus enhance portability. Further, the cart can incorporate a smart chip for identifying pre-packaged syringes of medication, to ensure that the proper medication is administered.

While the present invention has been illustrated by the description of embodiments thereof in considerable detail, it is not intended to restrict or limit the scope of the appended claims to such detail. Additional advantages and modifications will be readily apparent to those skilled in the art. Accordingly, departures may be made from such details without departing from the scope or spirit of the invention.

What is claimed is:

1. A system for use in the placement of a regional anesthesia block without the need of ancillary assistance, the system comprising:
    a) a nerve localization means for assisting an operator in locating a target nerve of a patient;
    b) a position assist arm for maintaining the position of the localization means over the target nerve once the target nerve has been located;
    c) an infusion device adapted to control anesthetic medication flow through a regional anesthesia needle;
    d) a foot pedal for controlling the flow of anesthetic medication through the infusion device, the foot pedal including an event button for recording a significant event and a picture button for creating a photograph of the significant event, wherein the buttons are operable via depression by the operator's foot;
    e) a portable battery for use either as backup when there is no standard electrical outlet available, or as a main source of power for all of the elements on the cart, thereby enhancing the portability of the system; and
    f) a cart for transporting the system from one area of a hospital or medical center to the room of a patient requiring a regional anesthesia block, wherein the combination of the nerve localization means, the position assist arm, the infusion device and the foot pedal allows the operator to be free to use both hands for manipulating the anesthesia needle during the regional anesthesia block procedure.

2. The system of claim 1, further comprising a control module for controlling communication between the infusion device and the foot pedal, the control module comprising an infusion control for inputting preset parameters of operation for the infusion device, and a pedal control for controlling operation of the foot pedal in accordance with the preset parameters.

3. The system of claim 2, wherein the infusion device is set to function at infusion pressures of between about 10 psi to about 20 psi, and at an infusion rate of between about 5 ml/min to about 15 ml/min.

4. The system of claim 2, wherein the infusion device is programmed to sound an alarm when infusion pressures are outside the preset parameters and then automatically slow, stop, or prevent initiation of infusion to avoid nerve damage from a possible intra-neural injection.

5. The system of claim 1, further comprising a video display device which can be coupled to the nerve localization means, the infusion device, an EKG monitor, a blood pressure cuff, a pulse oximeter, or a peripheral nerve stimulator to provide a real-time display during placement of the block.

6. The system of claim 5, wherein the nerve localization means is an ultrasound imaging system, and the video display device is a monitor which is coupled with the ultrasound imaging system to display a visual image of the target nerve.

7. The system of claim 1, further including a smart chip for identifying pre-packaged syringes of medication to ensure that the proper medication is administered.

8. A transportable regional anesthesia blockade system for performing a regional anesthesia block procedure, comprising:
    a) an ultrasound imaging system to assist an operator in locating a target nerve, the ultrasound imaging system including a central processing unit and an ultrasound transducer probe;
    b) a position assist arm for maintaining the position of the ultrasound transducer probe over the target nerve once the target nerve has been located;
    c) an infusion device for controlling anesthetic medication flow through a regional anesthesia needle, the infusion device including flexible tubing which leads from the infusion device to the anesthesia needle;
    d) a foot pedal for powering the infusion device, the foot pedal including a coupling cable which leads from the foot pedal to the infusion device, an event button for recording a significant event, and a picture button for creating a photograph of the significant event, wherein the buttons are operable via depression by the operator's foot;
    e) a video display device which can be coupled to the ultrasound imaging system, the infusion device, an EKG monitor, a blood pressure cuff, a pulse oximeter, or a peripheral nerve stimulator to provide a real-time display during placement of the block; and
    f) a cart for transporting the system from one area of a hospital or medical center to the room of a patient requiring a regional anesthesia block, wherein the combination of the ultrasound imaging system, the position assist arm, the infusion device and the foot pedal allows the operator to be free to use both hands for manipulating the anesthesia needle during the regional anesthesia block procedure.

9. The transportable regional anesthesia blockade system of claim 8, further comprising a control module for controlling communication between the infusion device and the foot pedal, the control module comprising an infusion control for inputting preset parameters of operation for the infusion device, and a pedal control for controlling operation of the foot pedal in accordance with the preset parameters.

10. The transportable regional anesthesia blockade system of claim 9, wherein the infusion device is set to function at infusion pressures of between about 10 psi to about 20 psi, and at an infusion rate of between about 5 ml/min to about 15 ml/min.

11. The transportable regional anesthesia blockade system of claim 9, wherein the infusion device is programmed to sound an alarm when infusion pressures are outside the preset parameters and then automatically slow, stop, or prevent initiation of infusion to avoid nerve damage from a possible intra-neural injection.

12. The transportable regional anesthesia blockade system of claim 8, wherein the video display device is a monitor which is coupled with the ultrasound transducer probe to display a visual image of the target nerve.

13. The transportable regional anesthesia blockade system of claim 8, further including a portable battery for use either as backup when there is no standard electrical outlet available, or as a main source of power for all of the elements on the cart, thereby enhancing the portability of the system.

14. The transportable regional anesthesia blockade system of claim 8, further including a smart chip for identifying pre-packaged syringes of medication to ensure that the proper medication is administered.

15. A method of performing a regional anesthesia blockade procedure without the need for ancillary assistance, the method comprising the steps of:
    a) providing a transportable regional anesthesia blockade system to an operator, the system comprising an ultrasound imaging system to aid in locating a target nerve, a position assist arm for maintaining the position of the ultrasound imaging system over the target nerve once the target nerve has been located, an infusion device for controlling anesthetic medication flow through a regional anesthesia needle, a foot pedal for powering the infusion device, the foot pedal including an event button for recording a significant event and a picture button for creating a photograph of the significant event, a video display device, and a cart for transporting the system within a hospital or medical center to the room of a patient requiring a regional anesthesia block;

b) transporting the transportable regional anesthesia blockade system via the cart to the patient;

c) locating a target nerve of the patient via the ultrasound imaging system;

d) stabilizing the ultrasound imaging system over the located target nerve by affixing the ultrasound imaging system to the position assist arm;

e) inserting a regional anesthesia needle into an injection site at or near the target nerve;

f) operating the foot pedal to inject medication from the infusion device through the regional anesthesia needle and into the injection site;

g) coupling the video display device to the ultrasound imaging system to provide a real-time display during placement of the block;

h) recording a significant event via depression of the event button by the operator's foot; and i) creating a photograph of the significant event via depression of the event button by the operator's foot.

16. The method of claim 15, wherein the infusion device is programmable to sound an alarm when infusion pressures are outside preset parameters and then automatically slow, stop, or prevent initiation of infusion to avoid nerve damage from a possible intra-neural injection.

* * * * *